United States Patent [19]

Tsukada et al.

[11] Patent Number: 5,035,505
[45] Date of Patent: Jul. 30, 1991

[54] ATOMIC ABSORPTION SPECTROSCOPY PHOTOMETER

[75] Inventors: Masamichi Tsukada, Ibaraki; Hayato Tobe, Mito, both of Japan

[73] Assignee: Hitachi, Ltd., Tokyo, Japan

[21] Appl. No.: 557,647

[22] Filed: Jul. 25, 1990

[30] Foreign Application Priority Data

Aug. 2, 1989 [JP] Japan ................................ 1-199408

[51] Int. Cl.⁵ .......................... G01J 3/10; G01N 21/74
[52] U.S. Cl. ..................... 356/319; 356/312; 356/307
[58] Field of Search ............... 356/311, 312, 315, 316, 356/319, 307, 326, 328

[56] References Cited

U.S. PATENT DOCUMENTS

| | | | |
|---|---|---|---|
| 4,669,879 | 6/1987 | Stockdale et al. | 356/312 |
| 4,867,562 | 9/1989 | Oishi et al. | 356/312 |
| 4,976,541 | 12/1990 | Scuitto et al. | 356/311 |

FOREIGN PATENT DOCUMENTS

| | | | |
|---|---|---|---|
| 63-292040 | 11/1988 | Japan. | |
| 119739 | 5/1989 | Japan | 356/311 |

Primary Examiner—F. L. Evans
Attorney, Agent, or Firm—Antonelli, Terry, Stout & Kraus

[57] ABSTRACT

An atomic absorption spectroscopy photometer comprising: sample atomizing means for heating to atomize a sample; a plurality of light sources disposed at a like number of light flux incidence positions for causing light having required wavelengths to enter the atomized sample; means for measuring the degrees of light absorption of a plurality of elements contained in the sample by detecting the fluxes of light which have passed through the atomized sample; a plurality of holder means for holding the plurality of light sources, the plurality of light sources being larger in number than the plurality of the light flux incidence positions; and means for setting required ones of the light sources of the plurality at the corresponding light flux incidence positions by moving the holder means.

16 Claims, 9 Drawing Sheets

ATOMIC ABSORPTION SPECTROSCOPY PHOTOMETER

BACKGROUND OF THE INVENTION

The present invention relates to atomic absorption spectroscopy photometers and more particularly to photometers which simultaneously analyze a multiplicity of elements contained in a sample.

In simultaneous atomic absorption analysis of a multiplicity of elements, a group of elements optimal or more suitable for simultaneous measurement is determined depending on various conditions such as the kind and purpose of a sample to be used or temperature conditions up to atomization of the respective elements contained in the sample. In atomic absorption spectroscopy, a light source comprising a hollow cathode lamp corresponding to each of elements to be analyzed is required. Thus, hollow cathode lamps which are the same in number as the elements to be analyzed simultaneously are required to be provided in a light source section.

Conventionally, such a light source section includes a group of four hollow cathode lamps used simultaneously and disposed fixedly at positions where fluxes of light enter the sample, as disclosed, for example, in Japanese Patent Publication JP-A-63-292040.

In the above conventional techniques, a combination of elements to be simultaneously measured changes depending upon various conditions. For example, (1) in the case of canned drinks, a combination of elements to be measured simultaneously changes depending on the field of the sample; for example, four elements of aluminum, iron, copper and zinc (For Sanitation Act); in the case of a photoresist solution, a combination of three elements, namely, sodium, iron and potassium. (2) A combination of elements to be simultaneously measured changes depending on heating temperature. A combination of aluminum and lanthanum which are atomized at a high temperature of about 3000° C.; a combination of cadmium and mercury which are atomized at 1500° C. (3) A combination of elements to be simultaneously measured changes depending on the difference in density between elements contained in a sample to be measured. (4) A combination of elements to be simultaneously measured changes depending on the presence of various additives; namely, an additive for preventing bumping of a sample during heating or oxidants and sublimators for obtaining better absorption signals at atomization. The conventional techniques do not allow for provision and disposition of hollow cathode lamps corresponding to respective elements depending on various changes in the conditions.

Thus, when a combination of and conditions of elements to be simultaneously measured are to be changed, the hollow cathode lamps and holders, which supply electric currents to the corresponding lamps, used so far are required to be replaced manually with appropriate ones.

SUMMARY OF THE INVENTION

It is an object of the present invention to provide an atomic absorption spectroscopy photometer which results in high analysis efficiency and which is capable of easily changing a combination of light sources corresponding to elements to be measured.

It is another object of the present invention to provide an atomic absorption spectroscopy photometer which, whether a sample contains elements which are larger in number than the elements measurable simultaneously or there are pluralities of combinations of elements measurable simultaneously, is capable of sequentially measuring those elements automatically.

In order to achieve the above objects, the present invention provides an atomic absorption spectroscopy photometer with a plurality of light flux incidence positions where fluxes of light enter a sample atomizing unit, comprising light sources larger in number than the light flux incidence positions, means for selecting a combination of light sources for corresponding to a like number of elements to be measured or holders for receiving the respective light sources, and means for moving the light sources or holders of the selected combination to the light flux incidence positions.

In addition, in order to sequentially measure automatically elements larger in number than the elements measurable simultaneously or different combinations of elements, the present invention provides an atomic absorption spectroscopy photometer which comprises means for selecting among a multiplicity of light sources a combination of light sources or holders corresponding to designated elements, and means for moving the light sources of the selected combination sequentially to the light flux entrance positions.

Also, the present invention provides an atomic absorption spectroscopy photometer which comprises means for storing data on designated elements larger in number than the elements measurable simultaneously, and means for selecting among a multiplicity of light sources or their holders a combination of light sources or their holders, on the basis of the stored data on designated elements, and means for moving the light sources of the selected combination sequentially to the light flux entrance positions, on the basis of the designated elements data of which are stored.

According to the present invention, any combination of light sources corresponding to a like number of elements to be measured simultaneously is selected and the light sources of the selected combination are disposed at light flux incidence positions. Thus, when the elements to be measured are to be changed, a combination of light sources for a new combination of elements is easily obtained without constraint on light sources fixedly disposed beforehand to thereby perform an atomic absorption spectroscopy very efficiently.

A combination of light sources corresponding to elements larger in number than the elements measurable simultaneously or a different combination of elements is beforehand selected among a plurality of light sources and the light sources of the selected combination are moved sequentially to the light flux incidence positions and disposed there. Thus this series of analyzing operations can be performed automatically.

DESCRIPTION OF THE PREFERRED EMBODIMENTS

One embodiment of the present invention will be described with respect to FIGS. 1-5.

Figure 1:
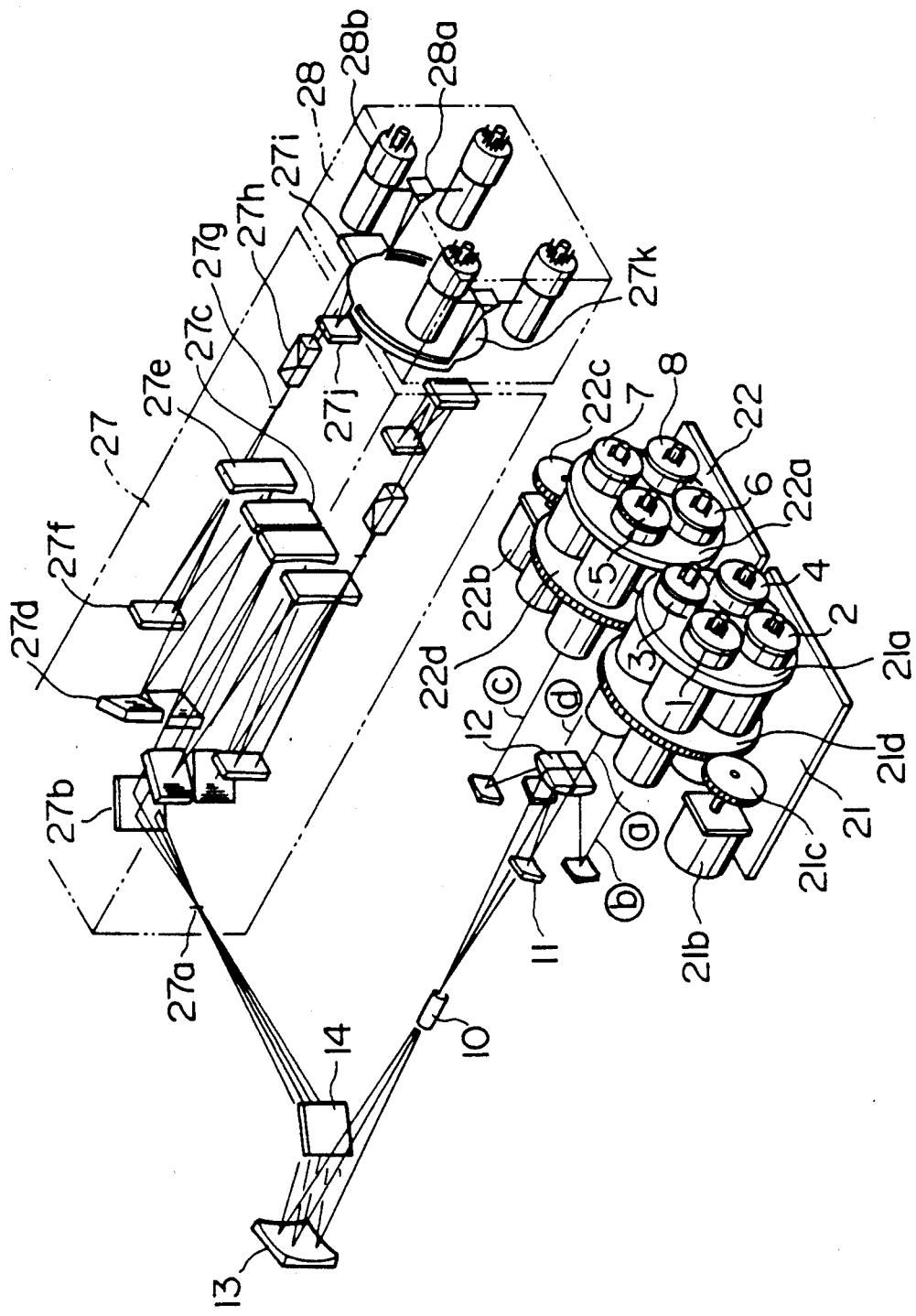
FIG. 1 is a schematic view of an optical system of an atomic absorption spectroscopy photometer according to one embodiment of the present invention.

FIG. 1 shows one embodiment of an atomic absorption spectroscopy photometer according to one embodiment of the present invention and, especially, shows an optical system for simultaneous analysis of four elements. As shown, the present optical system include four optical axes a , b , c and d on which are disposed hollow cathode lamps 3, 4, 5 and 6, the fluxes of light from which are focused by four spherical mirrors 11 and a spherical mirror 12 onto a cylindrical graphite cuvette 10 comprising an atomizing furnace and then guided to a spectroscope 27 through a spherical mirror 13 and a plane mirror 14 which is provided to reduce an off-axis angle.

The four fluxes of light guided to the spectroscope 27 are entered through a common incident slit 27a into a plane mirror 27b where the fluxes of light are divided into two upper fluxes of light and two lower fluxes of light which are then separated by a pair of collimators 27c into two upper fluxes of light and two lower fluxes of light; four independent parallel fluxes of light in all, which are then diverged by four corresponding diffraction ratings 27d again into two upper fluxes of light and two lower fluxes of light which are output through a pair of outlet slits 27g by a pair of camera mirrors 27e and a pair of folded plane mirrors 27. These output fluxes of light are guided to a photodetection unit 28 through a pair of Wollaston polarizing prisms 27h and a chopper 27k.

Figure 2:
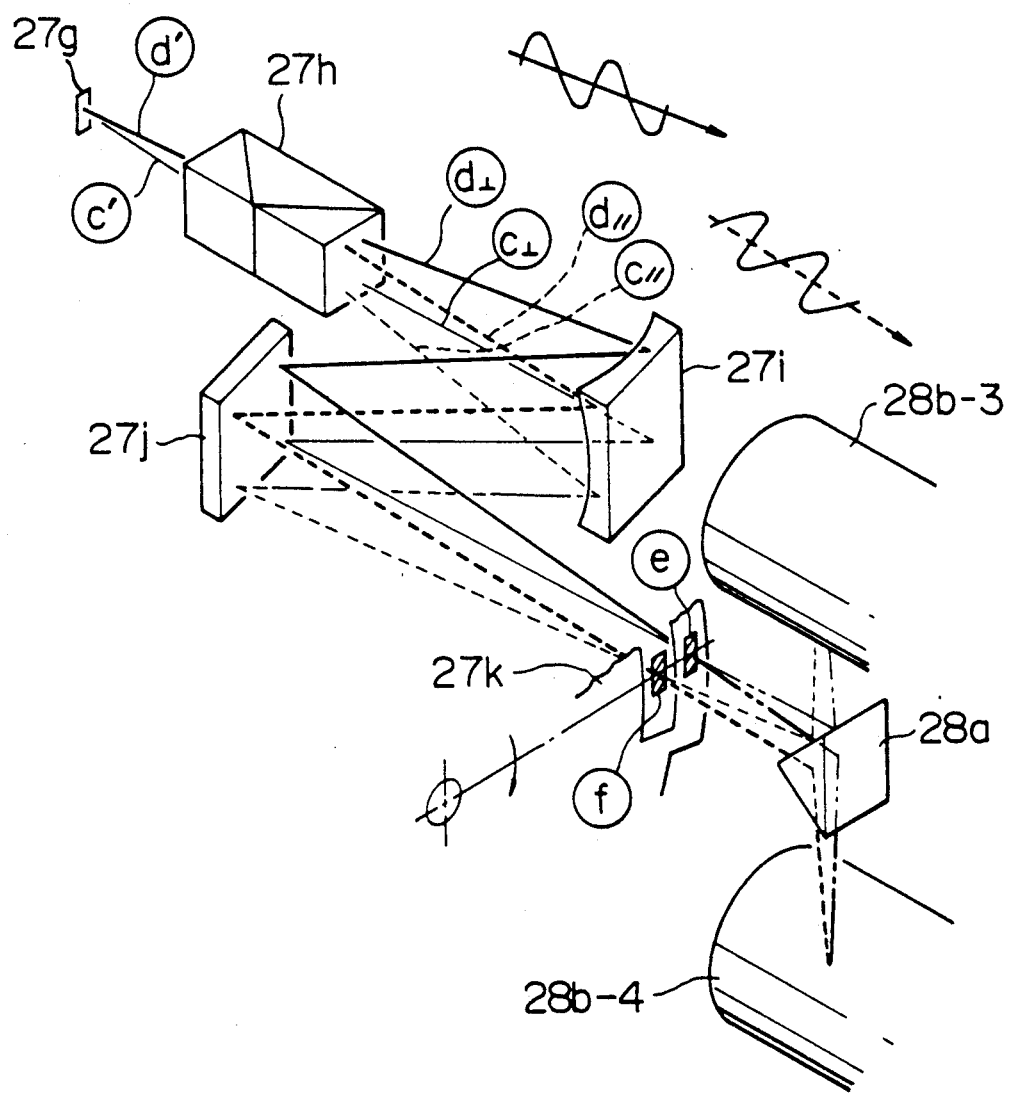
FIG. 2 is an enlarged perspective view of part of FIG. 1.

A detailed structure comprising the outlet slits 27g to the photodetection unit 28 will be described with respect to FIG. 2, in which upper and lower fluxes of light c' and d' having optical axes c and d and selected wavelengths radiated from the slit 27g are polarized into transversal waves c $\parallel$ and d $\parallel$ vibrating horizontally and longitudinal waves c $\parallel$ and d$\perp$ vibrating longitudinally when they pass through the Wollaston polarizing prism 27h. The transversal and longitudinal waves correspond to sample and reference fluxes of light, namely, fluxes of light polarized parallel and normal, respectively, to the magnetic field in background correction (JIS K0121) by Polarization Zeeman Method, and are alternately discriminated by the chopper 27k through the spherical mirror 27i and the plane mirror 27j and then guided to the photodetection unit 28. The spherical and plane mirrors 27i and 27j are arranged so as to focus an image of the slit 27g onto a rotational surface of the chopper 27k such that images f and e of the transversal and longitudinal waves, respectively, are spaced and that portion of the prism 27k where the transversal and longitudinal light components are separated is focused onto a photodetection face of a photomultiplier 28b. The transversal and longitudinal waves c $\parallel$ and c$\perp$ discriminated by the chopper 27k are alternatively deflected upwardly by a roof-like plane mirror 28a and detected by a photomultiplier 281-3. The transversal and longitudinal waves d $\parallel$ and d$\perp$ discriminated by the chopper 27k are alternatively deflected downwardly by the plane mirror 28a and discriminated by a photomultiplier 281-4. These detected waves are converted to electrical signals for signal processing. While the above structure is described as being directed to the two optical axes c and d , a similar structure is used for the optical axes a and b .

In FIG. 1, fluxes of light from the hollow cathode lamps 3-6 corresponding to the respective elements to be measured simultaneously are absorbed in accordance with the contents of elements, contained in the atom vapor of the sample when they passes through the graphite cuvette, the fluxes of light having respective wavelengths inherent to the target elements are selected by the spectroscope 27 and detected by the respective photomultipliers in the photodetector 28. Thus the respective densities of the target elements are calculated from the corresponding quantities of absorption of the atom vapor.

A first and a second lamp switching unit 21 and 22 constitute a part of the features of the present invention and supply and dispose to and on four optical axes a , b , c and d hollow cathode lamps corresponding to elements which satisfy respective purposes of measurement. The lamp holders 21a and 22a of cathode lamps 1-4 and 5-8, respectively, and are reversibly rotated independently through gears 21c, 21d and 22c, 22d by pulse motors 21b and 22b, respectively. In FIG. 1, the first lamp switching unit 21 is responsible for the optical axes a , b on which the hollow cathode lamps 3 and 4, respectively, are disposed. Similarly, the second lamp switching unit 22 is responsible for the optical axes c , d on which the hollow cathode lamps 5 and 6, respectively, are disposed.

Figure 3:
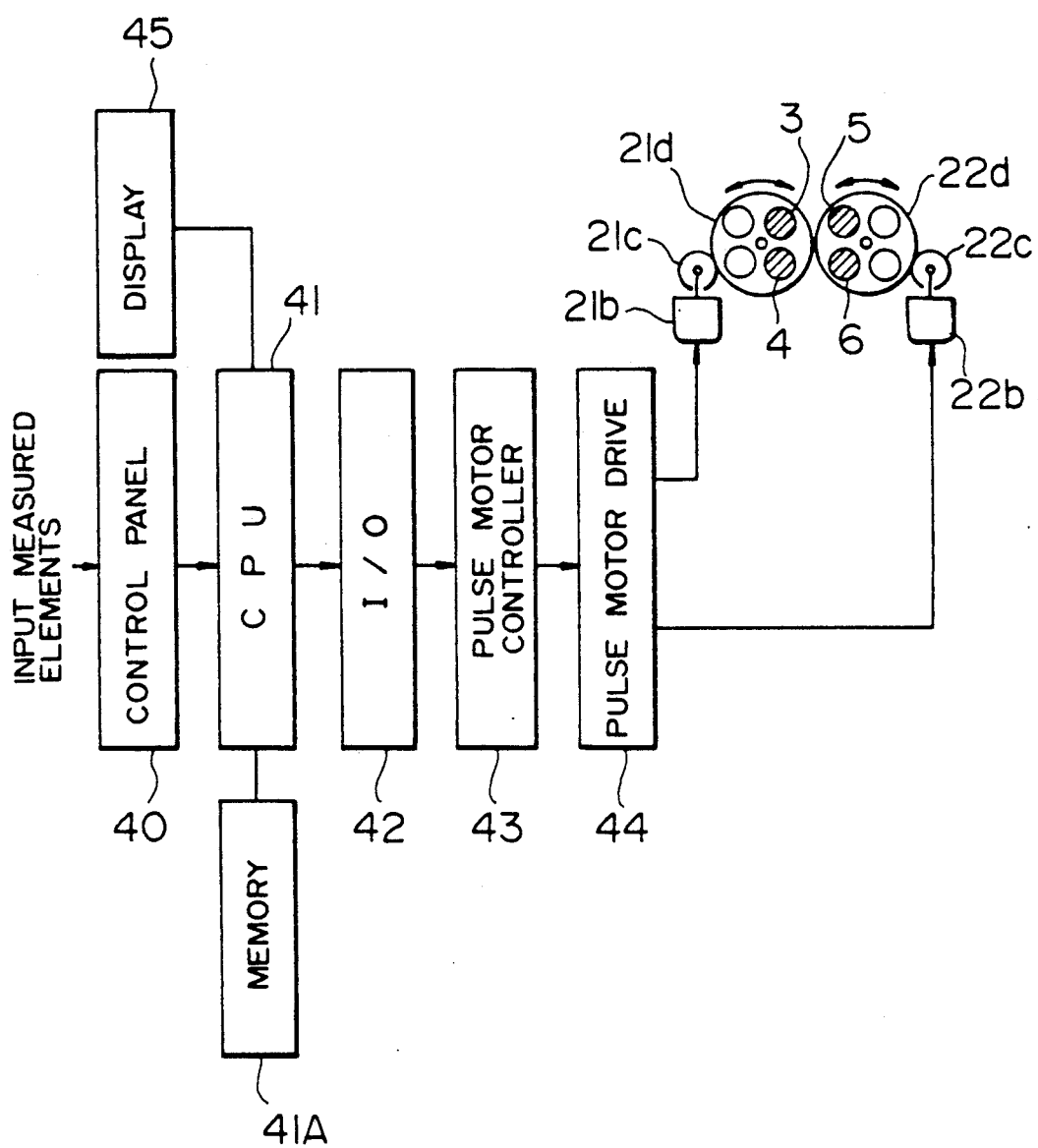
FIG. 3 is an overall schematic of an atomic absorption spectroscopy photometer according to the embodiment of the present invention.

FIG. 3 shows the overall structure of one embodiment of the inventive photometer which analyzes four elements simultaneously. Up to a process which disposes on the optical axes the corresponding hollow cathode lamps for the elements to be measured will be described with respect to FIG. 3. First, the measurer inputs at control panel 40 data on the names of elements to be measured. A CPU 41 selects an optimal combination of elements among the input data on the names of elements on a dialog basis under conditions inherent to the elements listed in Table 1 stored in a memory 41A in accordance with a flowchart of FIG. 4. It further instructs the pulse motors 21b and 22b of the lamp switching units 21 and 22 to dispose the corresponding hollow cathode lamps on the predetermined optical axes via an I/O interface 42, a pulse motor controller 43 and a pulse motor drive 44. Thus, the pulse motors 21b and 22b rotate separately to drive the lamp holders 21a and 22a through the gears 21c, 21d and 22c, 22d to thereby dispose on the optical axes the hollow cathode lamps corresponding to the elements put beforehand in the lamp holders.

TABLE 1

| NO. | ELEMENT SYMBOL | WAVE-LENGTH (nm) | LAMP CURRENT (mA) | ASHING TEMP | ATOMIZING TEMP |
| --- | --- | --- | --- | --- | --- |
| 1 | Ag | 328.1 | 5.0 | 490 | 2400 |
| 2 | Al | 309.3 | 7.5 | 710 | 3000 |
| 3 | As | 193.7 | 18.0 | 430 | 2800 |
| 4 | Au | 242.8 | 10.0 | 440 | 2700 |
| 5 | Ba | 553.6 | 12.5 | 720 | 2900 |
| 6 | Be | 234.9 | 10.0 | 610 | 2600 |
| 7 | Bi | 223.1 | 10.0 | 300 | 2000 |
| 8 | Ca | 422.7 | 7.5 | 580 | 2700 |
| 9 | Cd | 228.8 | 6.0 | 280 | 1500 |
| 10 | Co | 240.7 | 10.0 | 620 | 2700 |
| 11 | Cr | 359.4 | 7.5 | 700 | 2900 |
| 12 | Cu | 324.8 | 5.0 | 600 | 2700 |
| 13 | Fe | 248.3 | 10.0 | 630 | 2700 |
| 14 | Ga | 294.4 | 10.0 | 360 | 2800 |
| 15 | Ge | 265.2 | 10.0 | 620 | 2800 |
| 16 | Hg | 253.7 | 6.0 | 150 | 1500 |
| 17 | In | 325.6 | 10.0 | 380 | 2000 |
| 18 | Ir | 264.0 | 10.0 | 520 | 2700 |
| 19 | K | 766.5 | 10.0 | 450 | 2500 |
| 20 | La | 550.1 | 12.5 | 1000 | 3000 |
| 21 | Li | 670.8 | 10.0 | 590 | 2700 |
| 22 | Mg | 285.2 | 10.0 | 500 | 2000 |
| 23 | Mn | 279.5 | 5.0 | 510 | 2500 |
| 24 | Mo | 313.3 | 10.0 | 1010 | 2700 |
| 25 | Na | 589.0 | 10.0 | 370 | 2000 |
| 26 | Ni | 232.0 | 10.0 | 670 | 2700 |
| 27 | Pb | 283.3 | 7.5 | 420 | 2000 |
| 28 | Pd | 244.8 | 10.0 | 730 | 2700 |
| 29 | Pt | 266.0 | 10.0 | 800 | 2700 |
| 30 | Rh | 343.5 | 10.0 | 810 | 2700 |
| 31 | Sb | 217.6 | 18.0 | 310 | 2500 |
| 32 | Se | 196.0 | 10.0 | 390 | 2400 |
| 33 | Si | 251.6 | 10.0 | 990 | 2800 |
| 34 | Sn | 224.6 | 10.0 | 400 | 2700 |
| 35 | Sr | 460.7 | 10.0 | 690 | 2700 |
| 36 | Te | 214.3 | 10.0 | 570 | 2600 |
| 37 | Ti | 364.3 | 10.0 | 900 | 3000 |
| 38 | Tl | 276.8 | 10.0 | 410 | 2300 |
| 39 | V | 318.4 | 10.0 | 910 | 3000 |
| 40 | Zn | 213.9 | 10.0 | 290 | 2000 |

Figure 4A:
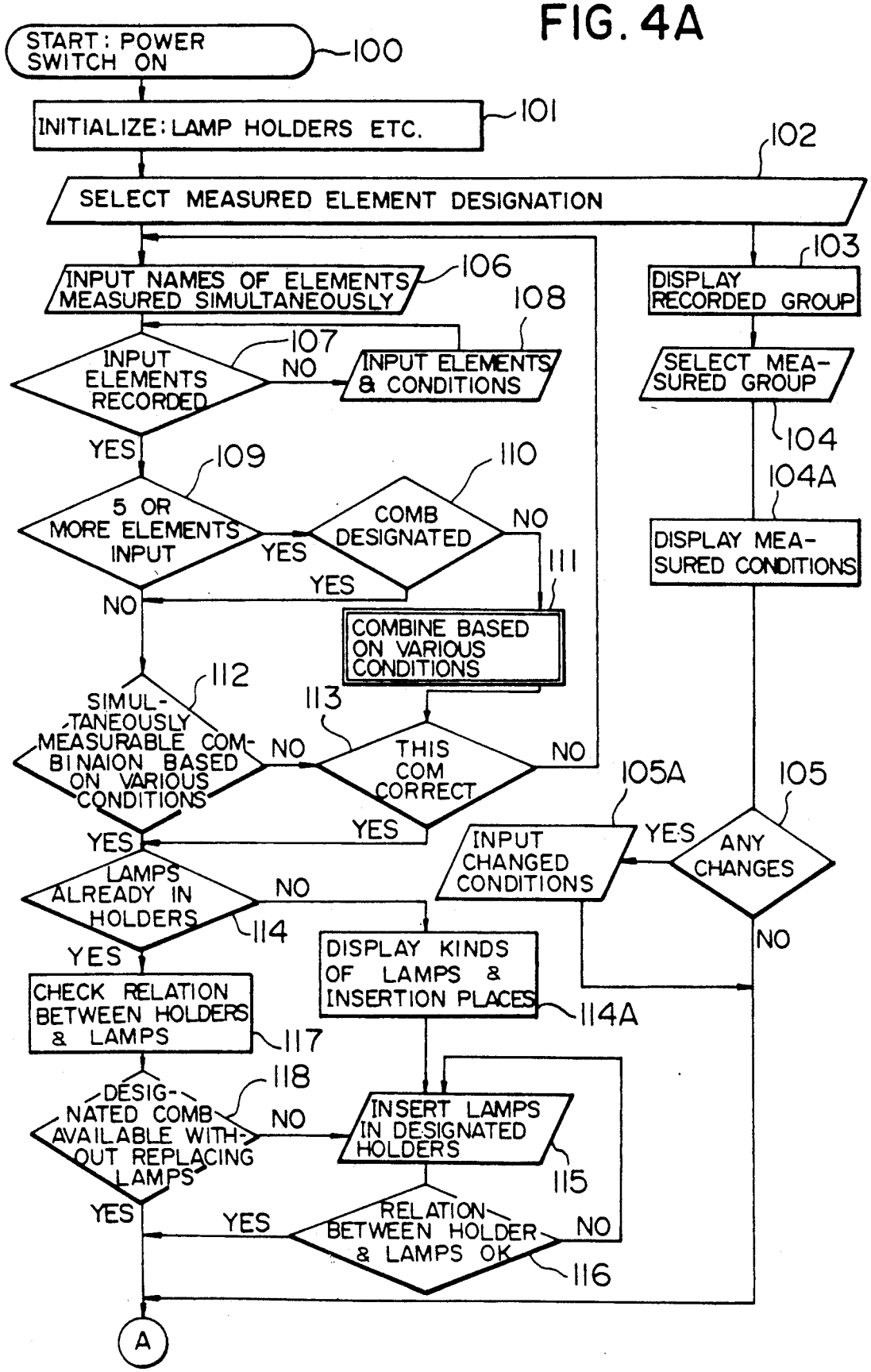
FIGS. 4A and 4B are a flowchart indicative of processing operations performed by the embodiment of the present invention.
Figure 4B:
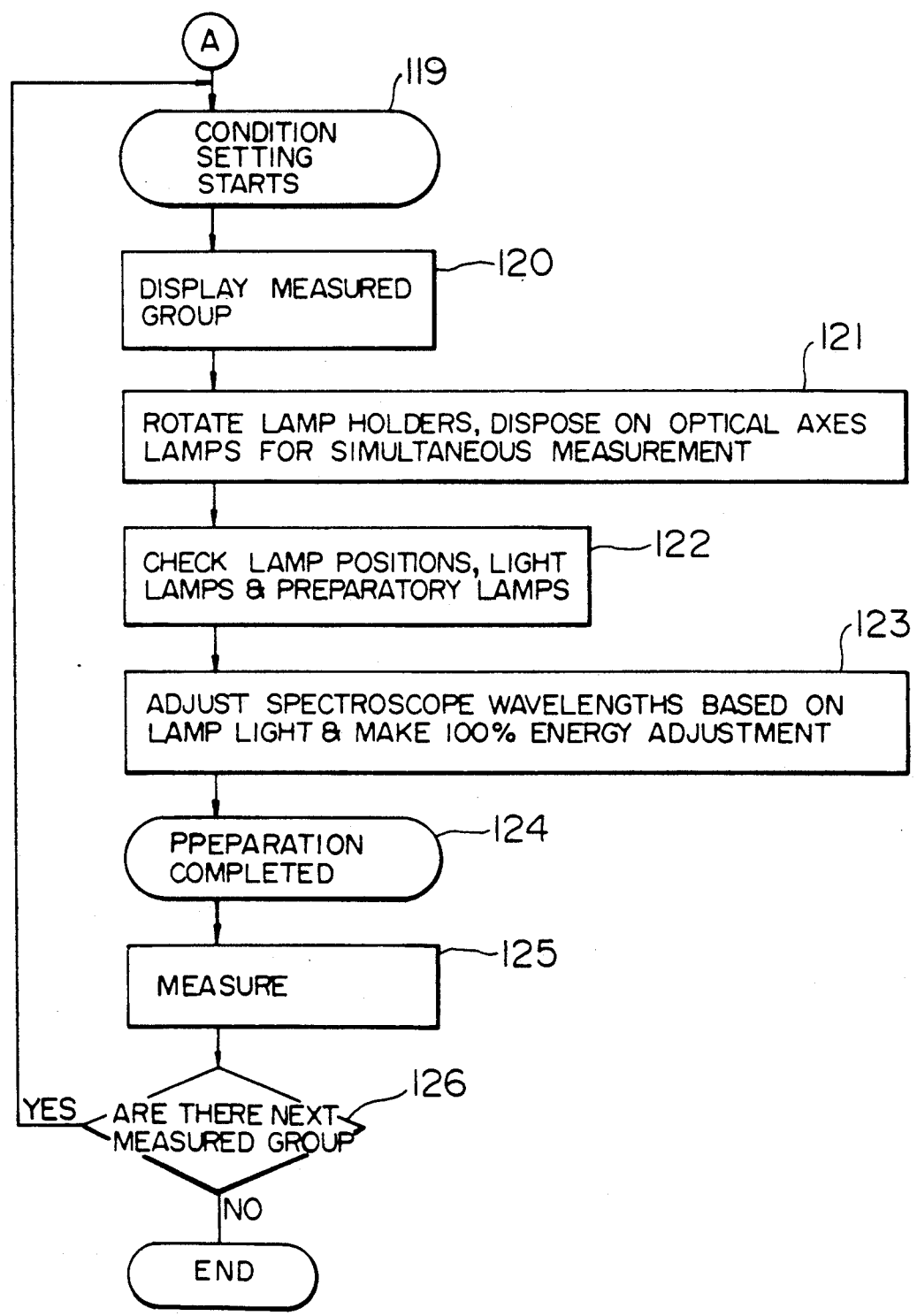

The above process will be described with respect to the flowchart of FIG. 4 indicative of the CPU operation. First, the measurer turns on a main switch (not shown) to power up the photometer (step 100) to thereby initialize same in preparation for measurement. At this time, CPU 41 is checked, the wavelength drive is set at its initial values, etc. The lamp switching units in the present invention are also set to their initial positions (step 101). When the series of preparatory operations have been completed, a step of setting measuring conditions starts. In this step, measurer inputs required data in a dialog basis using CPU 41 and display 45. In inputting the names of elements to be measured, the measurer selects either the use of a combination of elements recorded already in the photometer and to be measured simultaneously or newly inputting the names of elements to be measured simultaneously (step 102). The reason why the elements to be measured simultaneously are recorded beforehand is to eliminate a time for inputting data on the names of the elements in every measurement since there are some limited numbers of groups of elements combined in every measurement as in routine analysis.

When the use of a recorded combination of elements is selected, the recorded group is displayed (step 103). In this display, the names of elements of each group may be displayed, or the name of a sample such as for example, as "canned foods" or "sewage" may be displayed. If a target group is selected among those displayed ones and data on the selected group is input (step 104), display is made of the names of combined elements of the selected group and measuring conditions such as measurement time, measurement temperature, temperature change gradient or sampling frequency (step 104A). It is determined whether there are any changes in the displayed measuring conditions (step 105). If not, a condition setting operation starts immediately (step 119). If there are some changes in the conditions, a cursor is moved on the display screen to change required conditions (step 105A) and control passes to the condition setting operation (step 119).

When "input names of elements to be measured simultaneously" is selected at step 102, data on the names of elements to be measured simultaneously is input at step 106. It is confirmed whether the respective input names of elements are recorded in the memory 41A as measuring conditions shown in Table 1 (step 107). If not, or if the recording conditions are to be changed, the names of elements and those conditions are newly input (step 108). When it is confirmed that the measuring conditions for all the input names of elements are recorded (step 107), the number of input names of elements is checked (step 109). If the number of input names of elements is 5 or more, two measurements or more and hence division of the elements into two groups or more are required because up to four elements alone can be measured simultaneously in the present embodiment.

The measurer determines whether the elements for each group are beforehand designated when data on the names of elements are input at step 106 (step 110). If not, optimal combined elements are determined and grouped in accordance with ashing and atomizing temperatures which are conditions inherent to each elements in Table 1 stored in the memory 41A (step 111). All the elements of each group thus obtained are ashed at an ashing process. However, no atomization should occur at the ashing temperature.

Figure 5:
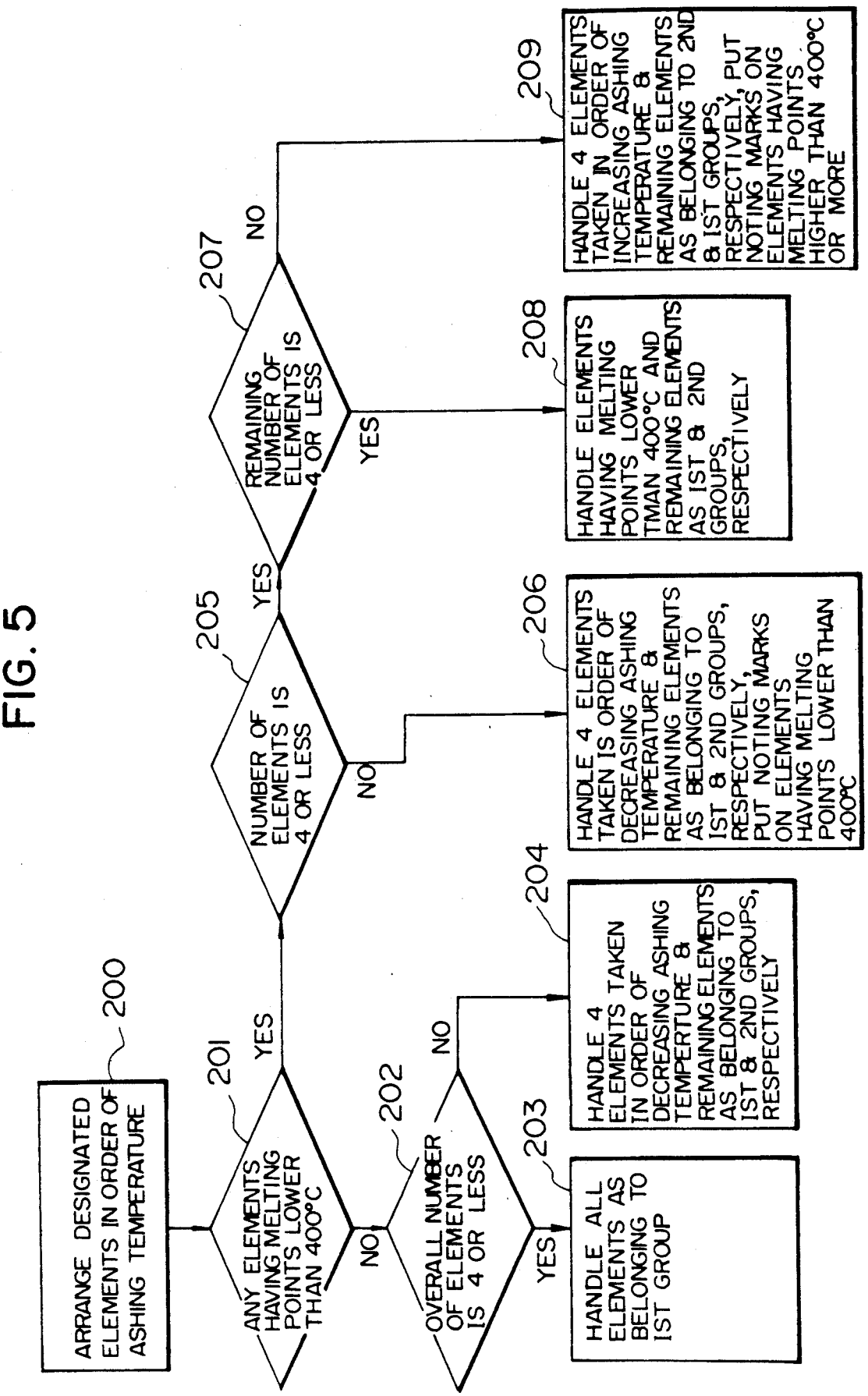
FIG. 5 is a flowchart indicative of the details of a step 111 of FIG. 4.

The contents of the step 111 will be described in more detail with respect to FIG. 5. Assume that the elements are grouped in accordance with ashing temperature and that the maximum number of groups is 2. All the elements of which are input are arranged in order of ashing temperature (step 200). It is checked whether elements having a low melting point lower than 400° C. are contained in the arranged elements (step 201). If not, it is checked whether all the number of elements is 4 or less (step 202), in which case all the elements are handled as belonging to one group (step 203). If the number of elements exceeds 4, four elements taken in order number of elements exceeds 4, four elements taken in order of decreasing ashing temperature are handled as belonging to a first group, and the remaining elements as belonging to a second group (step 204). If elements having a melting point lower than 400° C. are contained, it is checked whether the number of those elements is 4 or less (step 205). If not, four elements taken in order of decreasing ashing temperature are handled as belonging to a first group and the remaining elements as belonging to a second group, the elements of which are put a noting mark thereon (step 206) for measurer's determination in later steps. If the number of elements having a melting point lower than 400° C. is 4 or less, the number of remaining elements is checked (step 207) and elements having a melting point lower than 400° C. are handled as belonging to a first group and the remaining ones as belonging to a second group (step 208). If the number of elements having a melting point lower than 400° C. is 4 or less and the number of remaining elements exceeds 4 (steps 205–207), four elements taken in order of increasing ashing temperature are handled as belong to a second group and the remaining ones as belonging to a first group, the elements of which are put a noting mark (step 209) thereon for measurer's determination in later steps.

The ashing temperature of each group on a temperature program applied in actual measurement is set at the same value as the lowest one of the respective ashing temperatures which the elements of that group have ashing while the atomizing temperature of a group is set at the same temperature as the highest one of the atomizing temperatures which the elements of that group have to thereby heat and atomize all the elements of that group at a stroke.

The combination made at step 111 is displayed on the display 45 to cause the measurer to determine whether the combination as it is acceptable or not (step 113). If the combination is not acceptable, control returns to step 106 where the names of elements to be measured simultaneously start to be input again.

If the input number of elements is 4 or less (step 109) and the measurer specifies a group and combined elements of that group (step 110), the combination may be inappropriate due to conditions inherent to the elements (step 112). In this case, this fact is reported to the measurer for determining purposes (step 113).

When a combination of elements to be measured simultaneously is determined, lamps corresponding to the elements are required to be attached. If hollow cathode lamps are not attached in the corresponding lamp holders (step 114), kinds of hollow cathode lamps (elements) and the places where the corresponding lamp holders should be inserted are displayed (step 114A). The hollow cathode lamps are then inserted (step 115) and it is confirmed whether this insertion is made completely (step 116). This confirmation is made by checking whether a detector has detected with predetermined intensities the fluxes of light having predetermined wavelengths actually radiated in turns from the respective lamps. If the hollow cathode lamps are already inserted in the corresponding lamp holders, it is checked in a manner similar to step 116 where a lamp is inserted in each lamp holder and what element is represented by that lamp (step 117). It is checked whether a combination of elements required for measurement to be made this time can use the existing lamps and the existing positions where those lamps are inserted (step 118). Commands are given for all or some of the hollow cathode lamps to be replaced if necessary (step 115).

When the insertion of the hollow cathode lamps is terminated, the condition setting operation starts (step 119). Thus a sample is placed in the atomizing furnace 10 and a group of elements to be measured at a first time is displayed (step 120). The respective lamp holders are rotated to dispose on the respective optical axes the hollow cathode lamps corresponding to the elements (step 121). Electric currents are supplied to the corresponding lamps based on the conditions inherent to the respective lamps to light them (step 122). If there is a group of elements to be measured next, electric currents lower than the normally supplied ones are supplied to the lamps corresponding to the elements of that group for preparatory lighting to save the stable discharge awaiting time of the lamps (step 122).

When the lit state of the lamps is stabilized to some extent, the fluxes of light from the lamps are used to cause the respective spectroscopes to scan thereby set the wavelengths of light the analyzed resonant lines of the conditions inherent to the elements and to adjust the voltages applied to the respective photomultipliers each comprising a photodetector and hence to make a 100% energy adjustment which includes adjustment for providing a 100% energy output when light having a wavelength not absorbed by a sample is detected (step 123). In parallel with those preparatory operations related to the light sources, other preparatory operations such as setting the slit width, preparation of an automatic sample mechanism, gas control, and checking cooling water and various interlock functions are performed. When those preparatory operations are completed (step 124), the sample measuring step starts (step 125) to measure the first group. If two or more groups are designated (step 126), control returns again to the condition setting operation at step 119 to reiterate the series of preparing operations comprising the placement of the same sample as the preceding one in the atomizing furnace 10, disposition of the lamps corresponding to the elements of the next group on the respective optical axes, lighting the lamps, wavelength adjustment of the spectroscopes and 100%-energy adjustment.

Thus in correspondence to the elements set by the measurer and to be measured simultaneously, CPU 41 drives the pulse motors 21b, 22b to combine the lamps 1–8. If the number of elements to be measured simultaneously is 5 or more, the above operations are sequentially reiterated for the elements of each group to thereby measure the various kinds of elements automatically.

If a pair of lamp switching units 21, 22 each include four hollow cathode lamps to enable four optical axes or to measure four elements simultaneously as in the present embodiment, the number of combinations of lamps disposable on the four optical axes is 16, which is considered to suffice for regular measurement. If the numbers of combinations exceeds 16, CPU 41 selects a combination closest to that in the present lamp arrangement state and designates the minimum quantity of manual works which cannot be automated (lamp replacement at step 115), as shown also in the flowchart of FIG. 4. If there are many kinds of combinations of elements to be measured simultaneously, data on those respective combinations may be input beforehand to the CPU to be processed to thereby designate lamp holders and the places whether holders and the places where the holders are inserted to render the combinations effective.

Figure 6:
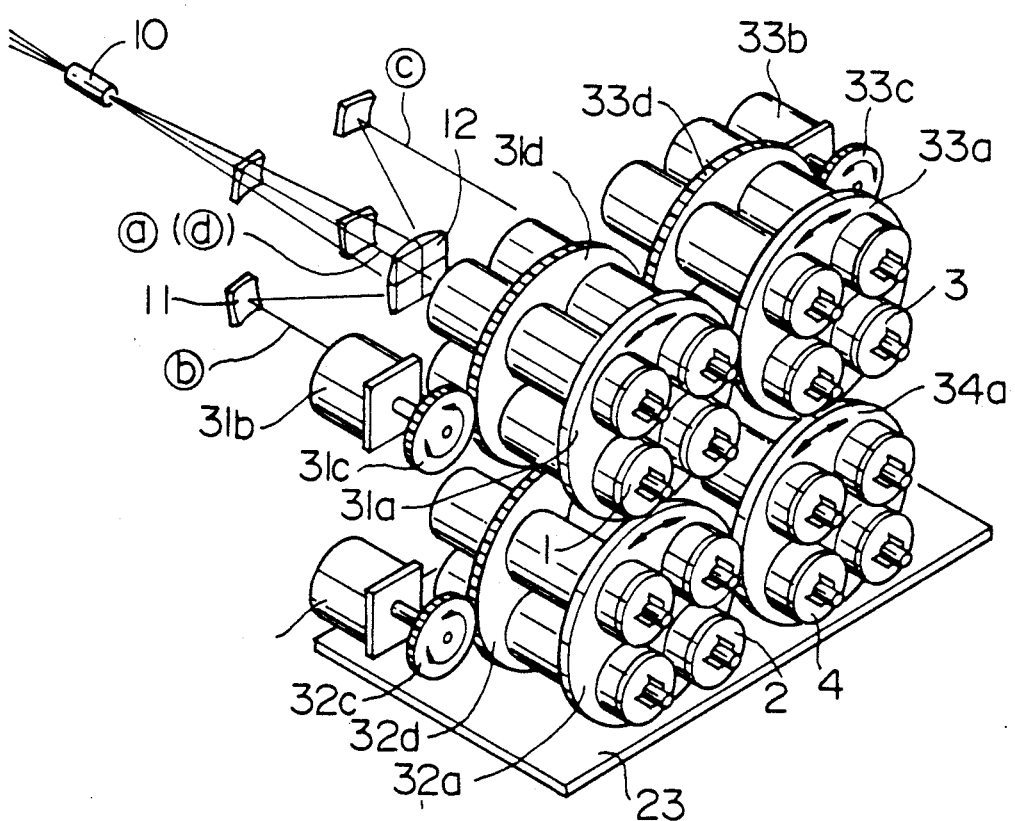
FIGS. 6-8 each are a perspective view of a light source section in another embodiment of the present invention.

While the embodiment using the two combined lamp switching units has been illustrated so far, lamp switching units, for example 31a–34a, may be provided which are the same in number as the optical axes so as to be responsible for the corresponding optical axes, as shown in another embodiment of FIG. 6, which shows that hollow cathode lamps 1, 2, 3 and 4 inserted in lamp holders 31a, 32a, 33a and 34a are disposed on optical axes a , b , c and d , respectively, with the optical axes a and d coinciding. In the present embodiment, the four lamp switching units each have four lamps inserted therein and hence 256 combinations of lamps are obtained.

Figure 7:
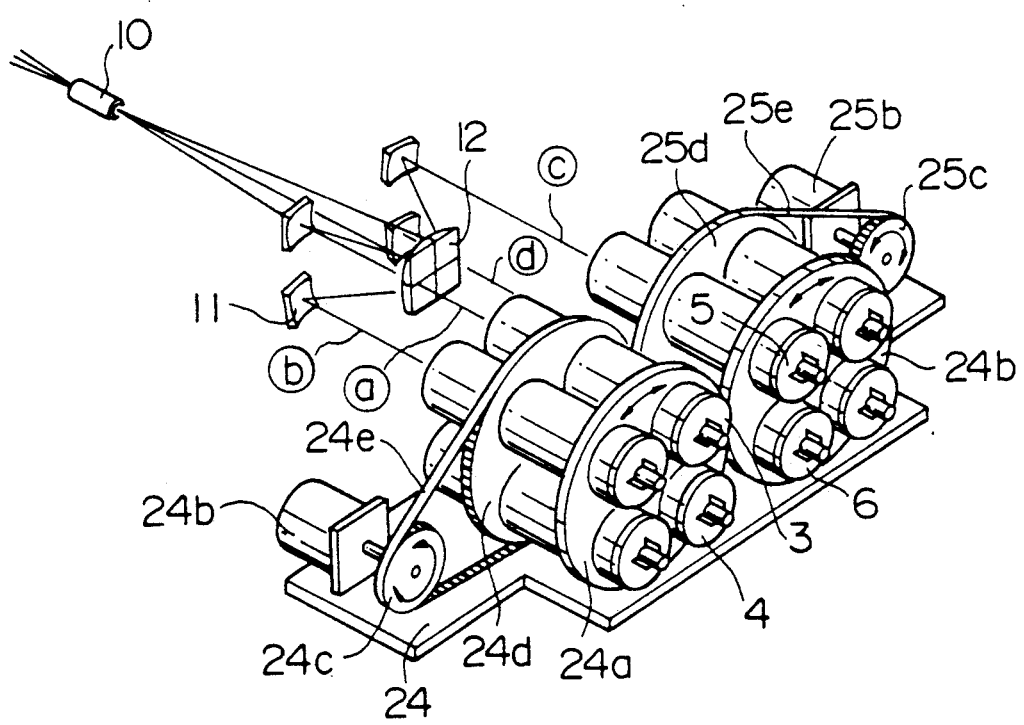

While the drive forces from the pulse motors have been shown and described as rotating the lamp holders through gears in the above embodiments, they may rotate the holders through timing belts, as shown in FIG. 7. By the drive force of the pulse motors 24b and 25b, pulleys 24c, 25c and 24d, 25d with gear teeth for the timing belts on their peripheries coupled through timing belts 24e, 25e and hence the lamp holders 24a, 25a are rotated to dispose the target lamps on the corresponding optical axes. FIG. 7 shows that the hollow cathode lamps 3, 4, 5 and 6 are disposed on the optical axes a , b , c and d , respectively.

Figure 8:
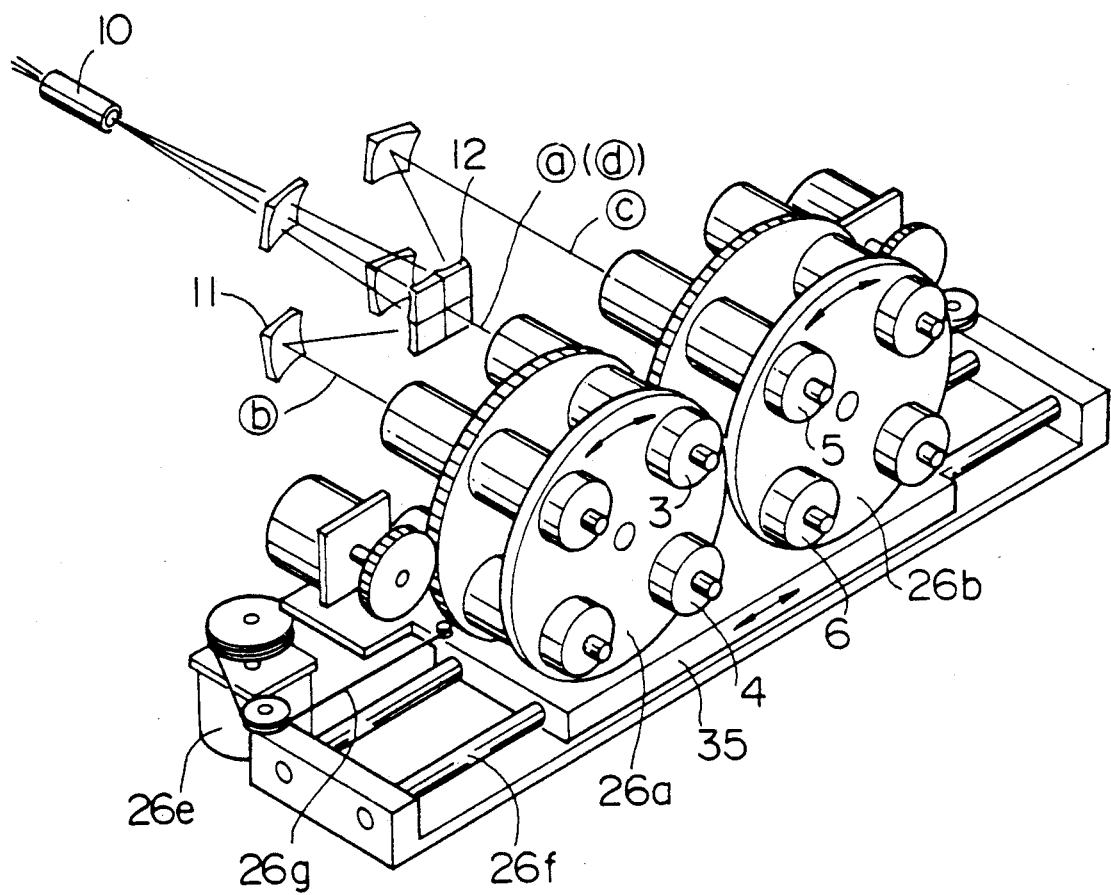

FIG. 8 shows a further embodiment which has a linear movement function in addition to the functions of the rotary lamp holder type lamp switching units. In FIG. 8, a rotary type lamp switching unit 35 is linearly reciprocated by the motor 26e through ropes 26g and sliding shafts 26f to dispose on the optical axes those hollow cathode lamps inserted in the holder 26a or 26b alone.

According to the present invention, a plurality of light sources corresponding to any combination of elements to be measured simultaneously are easily moved to light flux incidence positions, so that analysis of the elements is achieved efficiently with requiring no works such as replacement of the lamps. In addition, continuous measurement is achieved while changing a combination of elements to be measured simultaneously.

By designating beforehand the number of elements exceeding the number of elements to be measured simultaneously, those exceeding elements can sequentially be measured automatically.

Since no replacement of lamp holders which would otherwise be involved in the replacement of light sources is required, the inventive photometer is advantageous from a standpoint of safety.

We claim:

1. An atomic absorption spectroscopy photometer comprising:
    sample atomizing means for heating to atomize a sample;
    a plurality of light sources disposed at a like number of light flux incidence positions for causing light having required wavelengths to enter the atomized sample;
    means for measuring the degrees of light absorption of a plurality of elements contained in the sample by detecting the fluxes of light which has passed through the atomized sample;
    a plurality of holder means for holding the plurality of light sources, the plurality of light sources being larger in number than the plurality of the light flux incidence positions; and
    means for setting required ones of the light sources of the plurality at the corresponding light flux incidence positions by moving the holder means.

2. An atomic absorption spectroscopy photometer according to claim 1, further including:
    means for selecting a plurality of light sources corresponding to the plurality of elements in the sample to be measured; and
    wherein said setting means includes means for setting at the light flux incidence positions said plurality of light sources selected by said selecting means.

3. An atomic absorption spectroscopy photometer according to claim 2, wherein said selecting means includes:
    means for therein recording beforehand a plurality of predetermined groups of combined light sources; and
    means for selecting one of the plurality of groups recorded by said recording means.

4. An atomic absorption spectroscopy photometer according to claim 2, wherein said selecting means includes:
    means for inputting the names of elements to be measured simultaneously; and
    means for determining whether the combination of elements the names of which are input by said inputting means is measurable.

5. An atomic absorption spectroscopy photometer according to claim 4, wherein said selecting means further includes:
    means for determining whether the elements the names of which are input by said inputting means is larger in number than the light flux incidence positions; and
    means for preparing a plurality of groups of combined elements when said last-mentioned determining means determines that the elements the names of which are input are larger in number than the light flux incidence positions.

6. An atomic absorption spectroscopy photometer according to claim 2, wherein said selecting means includes:
    means for designating elements to be measured; and
    means for determining whether light sources corresponding to the elements designated by said designating means are held by said holder means.

7. An atomic absorption spectroscopy photometer according to claim 1, further including:
   means for setting a plurality of groups of combined light sources used for simultaneous measurement; and
   means for sequentially designating the measurements of the groups until the measurement of all the groups is completed.

8. An atomic absorption spectroscopy photometer according to claim 1, further including:
   means for designating the names of a plurality of elements to be measured;
   means for beforehand storing as a table a multiplicity of the names of elements and measuring conditions of the respective elements;
   means for reading from the table the measuring conditions of the plurality elements the names of which are designated by said designating means and determining whether simultaneous measurement is possible; and
   means for driving said light source setting means when said determining means determines that simultaneous measurement is possible.

9. An atomic absorption spectroscopy photometer according to claim 8, further including:
   means for setting the elements designated by said designating means and not recorded on said table, and the measuring conditions of those designated elements.

10. An atomic absorption spectroscopy photometer according to claim 1, further including:
    means for designating elements to be measured;
    means for determining whether light sources corresponding to the elements designated by said designating means are held by said holder means; and
    means for driving said setting means when said determining means determines that the light sources corresponding to the elements designated by said designating means are held by said holder means.

11. An atomic absorption spectroscopy photometer according to claim 10, further including:
    means for displaying the fact that the light sources corresponding to the elements designated by said designating means are not held by said holder means when said determining means determines so.

12. An atomic absorption spectroscopy photometer according to claim 11, wherein said displaying means includes:
    means for displaying kinds of light sources to be held and places where the light sources are held.

13. An atomic absorption spectroscopy photometer according to claim 1, wherein said holder means includes means held rotatably around an axis for disposing said light sources along the circumference of a circle having its center coincident with the axis.

14. An atomic absorption spectroscopy photometer according to claim 1, wherein said holder means includes a plurality of components each rotatable around an axis, each component holding a plurality of light sources along the circumference of a circle having its center coincident with the axis of that component.

15. An atomic absorption spectroscopy photometer according to claim 1, wherein said holder means includes a component supported slidable linearly.

16. An atomic absorption spectroscopy photometer according to claim 1, wherein said holder means includes a component supported slidable linearly and a plurality of components held on said slidable component and rotatable around an axis.

* * * * *